United States Patent [19]

Foley et al.

[11] 4,152,293

[45] May 1, 1979

[54] REDOX CATALYST OXIDANT, CATALYST AND POLYMERIZATION THEREWITH

[75] Inventors: Howard K. Foley, Cuyahoga Falls; David A. Hutchings, Stow; Paul H. Sandstrom, Tallmadge, all of Ohio

[73] Assignee: The Goodyear Tire & Rubber Company, Akron, Ohio

[21] Appl. No.: 937,039

[22] Filed: Aug. 25, 1978

Related U.S. Application Data

[63] Continuation of Ser. No. 784,884, Apr. 5, 1977, abandoned.

[51] Int. Cl.$^2$ .............................................. B01J 31/02
[52] U.S. Cl. ...................................... 252/426; 526/94; 526/93

[56] References Cited

U.S. PATENT DOCUMENTS

| | | | |
|---|---|---|---|
| 2,807,650 | 9/1957 | Webster et al. | 252/426 X |
| 3,009,962 | 11/1961 | Milas | 252/426 X |
| 3,515,705 | 6/1970 | Balitrand | 252/426 X |

*Primary Examiner*—Delbert E. Gantz
*Assistant Examiner*—William G. Wright
*Attorney, Agent, or Firm*—H. C. Young, Jr.

[57] ABSTRACT

The invention relates to a method of preparing a composite suitable as an oxidizing component in a redox aqueous emulsion polymerization initiator starting with the relatively harsh oxidation of p-diisopropylbenzene with oxygen and involving a manipulative separation procedure for obtaining the effective oxidizing component. The invention also relates to the oxidizing component, the redox polymerization initiator and to the aqueous emulsion polymerization of selected unsaturated monomers.

5 Claims, No Drawings

REDOX CATALYST OXIDANT, CATALYST AND POLYMERIZATION THEREWITH

This is a continuation of application Ser. No. 784,884, filed Apr. 5, 1977, now abandoned.

This invention relates to a diisopropylbenzene hydroperoxide composite suitable as an oxidant for interaction with a reducing agent, a method of preparing the composite, and the product thereof as a redox free radical polymerization initiator. The invention further relates to free radical polymerizing unsaturated organic compounds in an aqueous emulsion with such a redox initiator or catalyst.

The invention particularly relates to the preparation of the composite from a byproduct effluent from a process for producing diisopropylbenzene dihydroperoxide as an intermediate for producing hydroquinone.

The polymerization of various monomers in an aqueous emulsion is well known in the art. Indeed, synthetic rubber latices are conveniently prepared by the aqueous emulsion free radical polymerization of 1,3-butadiene or its copolymerization with other monomers such as styrene. Such well known emulsion polymerizations are generally conducted in an aqueous medium in the presence of a surfactant or emulsifier and a free radical initiator or catalyst of the redox type formed through the interaction between an oxidizing and a reducing agent. The reaction is generally shortstopped at a desired point after which the resultant polymer or copolymer is separated and subjected to washing, filtering and drying operations.

Monohydroperoxide type oxidizing agents for preparation of redox polymerization initiators have been widely accepted for use in aqueous emulsion free radical polymerizations. Exemplary are liquid mixtures of m- and p-diisopropylbenzene monohydroperoxide (U.S. Pat. No. 2,548,435). In practice, it is understood that such a hydroperoxide type initiator can be prepared by oxidizing diisopropylbenzene with oxygen under relatively mild conditions, including the manipulation of temperatures and/or conversion. The mild preparation conditions such as the combination of conversions of less than about 25 percent with oxidizing temperatures below about 100° C. are used in order to prevent appreciable formation of both the unwanted dihydroperoxides and oxidation byproducts, such as, for example, phenols, enols and ketones, a portion of which inhibit free radical polymerizations. In practice, it is understood that after the oxidation reaction, the low monohydroperoxide concentration is increased to about 50 percent by vacuum distillation of unoxidized hydrocarbon. Thus, the free radical polymerization grade hydroperoxide oxidant can be typically obtained in a relatively high purity form in a relatively straight-forward manner. In the mild preparation method, the bulk of the non-oxidant remainder is essentially the simple, unreacted, or unoxidized, diisopropylbenzene.

In contradistinction to the mild oxidation process, the process of more harshly oxidizing p-diisopropylbenzene to higher conversions is used for the purpose of preparing the dihydroperoxide for use as a hydroquinone precursor. Temperatures in the range of about 110° C. to 120° C. were used with a conversion to product in excess of 30 percent hydroperoxide equivalent resulting in an appreciable conversion to dihydroperoxide. A major portion of the dihydroperoxide was removed by a combination of crystallization/precipitation and filtration. The filtrate was a more concentrated monohydroperoxide with an attendant more concentrated byproduct content. The concentrated byproduct content was essentially of oxygenated compounds.

The remainder composite of monohydroperoxide and concentrated oxygenated byproducts was determined to be unsatisfactory for use in a redox catalyst for the aqueous emulsion copolymerization of 1,3-butadiene and isoprene.

In practice, the filtrate is recycled to the oxidizing step. In order to reduce byproduct build-up and concentration, a small portion of the recycle stream is purged by vacuum steam distillation with the distillate being returned to the recycle stream and the byproductrich distilland, also containing a portion of the monohydroperoxide, removed from the system.

The distilland was used as an oxidant for a redox initiator in an aqueous emulsion 1,3-butadiene/styrene polymerization. Although copolymerization occurred, the reaction had an xcessively long induction period, apparently due to residual reaction inhibitors. Thus, the distilland was found to be inadequate for optimum performance equivalent to the monohydroperoxide oxidant obtained by mildly oxidizing p-diisopropylbenzene.

It is important to appreciate that the induction period is an important part of the overall polymerization reaction. The induction period itself is a period of time preceding the onset of polymerization in which no conversion of monomer is observed and is especially noticeable when the quality of hydroperoxide is not high. Various amounts of inhibiting species are apparently formed in the harsh oxidation of diisopropylbenzene and subsequent processing, which yields a mixture of mono- and dihydroperoxides, as well as other oxidation products, one or more of which is a polymerization inhibitor.

Indeed, it is desired to convert the distilland composite product derived from the more harsh oxidation reaction to an oxidant substantially equivalent to the product of the mild oxidation reaction in terms of aqueous emulsion polymerization induction period.

Therefore, it is an object of this invention to provide an efficient oxidant for a redox catalyst from the composite derived from harshly oxidized p-diisopropylbenzene, a method for its preparation, the redox catalyst itself, and the copolymerization therewith of 1,3-butadiene and styrene.

In accordance with this invention it was discovered that a composite suitable for use as an oxidizing component in a redox aqueous emulsion polymerization initiator is a composite prepared by (A) obtaining the oxidation product of reacting p-diisopropylbenzene with oxygen at a temperature in the range of about 105° C. to about 120° C., preferably about 105° C. to about 115° C., said product comprised of a mixture of p-diisopropylbenzenemonohydroperoxide, p-diisopropylbenzenedihydroperoxide, unreacted p-diisopropylbenzene, and oxygenated byproducts containing aqueous emulsion diene polymerization inhibitors, (B) removing by a separation procedure, selected from at least one of crystallization and fractionation followed by subsequent filtration, a major portion of said p-diisopropylbenzenedihydroperoxide, and treating a portion of the filtrate by fractionation to remove p-diisopropylbenzene and a portion of said p-diisopropylbenzene monohydroperoxide distillate to effect a concentration of the remainder as a distilland having an equivalent monohydroperoxide content by ASTM No. E-298-68 in the range of about 70 percent to about 90 percent comprised, by weight of about 45 to about 65, preferably about 50 to about 60, percent p-diisopropylbenzene monohydroperoxide, about 5 to about 15, preferably about 5 to about 10, percent p-diisopropylbenzenedihydroperoxide and about 10 to about 30, preferably about 15 to about 25, percent oxygenated byproducts, (C) mixing with 100 parts by weight of said remainder distilland about 50 to about 400 parts by weight of at least one liquid, non-polar saturated hydrocarbon containing 5 to about 20, preferably 5 to 10, carbon atoms to form a solid/liquid two-phase product, (D) recovering said liquid phase, (E) treating 100 parts by weight of said liquid phase by mixing therewith about 50 to about 400 parts by weight of an aqueous sodium or potassium hydroxide solution containing about 0.5 to about 15 weight percent sodium or potassium hydroxide to form an organic/aqueous two-phase product, (F) recovering said organic phase, (G) treating the recovered organic phase one to three times with a dilute aqueous sodium hydroxide solution containing about 1 to about 4 weight percent sodium hydroxide to form a second organic-/aqueous two-phase product and (H) recovering said final organic phase.

In the practice of this invention, it is preferred that in step (A) the p-diisopropylbenzene is oxidized to a sufficient conversion that the product has about 40 to about 70 percent hydroperoxide content.

In the practice of this invention it is preferred that in step (B) the fractionation procedure be used whereas the remainder is obtained as a distilland where the fractionation is conducted to a pot temperature in the range of about 70° C. to about 110° C. In the practice of step (B), as the conversion proceeds, the dihydroperoxide tends to naturally precipitate out in the nature of a crystallization. It's removal can be enhanced through filtration.

In the further practice of this invention it is preferred that in step (C) the solid/liquid two-phase product is prepared by mixing said remainder with the saturated hydrocarbon at a temperature in the range of about 15° C. to about 50° C.

Representative of various saturated hydrocarbons for the operation of step (C) are paraffin-type hydrocarbons such as n-hexane, isohexane, n-heptane, isoheptane, n-octane and isooctane, and n-decane, as well as cyclic saturated hydrocarbons such as cyclopentane, cyclohexane, cycloheptane and cyclooctane. The paraffin-type saturated hydrocarbons are preferred of which n-octane is especially preferred for the operation of this invention. An important feature of step (C) is that a non-polar saturated hydrocarbon is applied to modify the polarity of the system so that the subsequent dilute caustic treatment is effective in removing the aqueous emulsion polymerization inhibitors.

The liquid phase can conveniently be recovered in step (D) by filtration. In step (E) it is preferred that the treatment is effected with adequate mixing of the aqueous caustic and recovered organic liquid phases at a temperature in the range of about 15° C. to about 50° C. and the system allowed to then equilibrate to an organic/aqueous two-phase product. The organic phase can then be simply withdrawn in step (F) by draining or decanting.

In the practice of this invention, it is preferred that the organic phase be washed in step (G) one to three more times with the dilute caustic solution as it was done in step (E) and recovered in step (H) as it was done in step (F) in order to more completely remove aqueous emulsion polymerization inhibitors.

It is important to appreciate in the practice of this invention that the oxidant for the redox catalyst is prepared by first, more harshly oxidizing p-diisopropylbenzene which forms unwanted byproducts and then concentrating such byproducts while refining the overall product to obtain the monohydroperoxide. In the fraction step used for recovering the monohydroperoxide, the oxygenated byproducts can be, in part, converted to other forms. At least a portion of the resulting concentrated byproducts in the monohydroperoxide have been generally found to be substantially inhibiting with regard to free radical formation for aqueous emulsion polymerization. Such byproducts can contain primarily phenols, enols and ketones, such as at least about 50 weight percent and more generally at least about 80 weight percent of such materials. The byproducts can be components attached to one end of the p-diisopropylbenzene while a monohydroperoxide constituent is attached to the other end. Alternatively, such components can be attached solely to a p-diisopropylbenzene molecule.

Typically, said byproducts comprise a mixture containing at least two compounds selected from p-isopropyl acetophenone, 2-(4-isopropylphenyl)-2-hydroxyperoxy propane, 2-(4-isopropylphenyl)-2-propanol, 1,4-diacetyl benzene, 4-($\alpha$-methyl-$\alpha$-hydroxyperoxyethyl)acetophenone, 4-($\alpha$-methyl-$\alpha$-hydroxyethyl)acetophenone, 1,4-Bis(1-methyl-1-hydroperoxyethyl)benzene, 1-($\alpha$-methyl-$\alpha$-hydroxyperoxyethyl)-4-($\alpha$-methyl-$\alpha$-hydroxyethyl)benzene, and 1,4-Bis(1-methyl-1-hydroxyethyl)benzene.

In the preparation of the oxidant portion of the redox catalyst the p-diisopropylbenzene is first preferably oxidized with oxygen to a conversion normally considered to be more favorable to the production of the dihydroperoxide and to be excessive for producing good purity p-diisopropylbenzene monohydroperoxide with minimal attendant byproduct formation. The product thereof is then treated to remove a major portion of p-diisopropylbenzene dihydroperoxide and unreacted p-diisopropylbenzene as well as a minor portion of the monohydroperoxide. The dihydroperoxide can be substantially removed from the product, for example, by conventional crystallization and/or fractionation techniques. The unreacted p-diisopropylbenzene can be removed by fractionation as a distillate, although a portion of its monohydroperoxide will normally be removed also.

As a result in such a fractionation, the normally unwanted byproducts are concentrated as a composite in the monohydroperoxide distilland in the bottom of the fractionation system.

If the untreated distilland or the alcohol diluted distilland is used as the oxidant in redox initiated emulsion copolymerization of 1,3-butadiene and styrene, an induction period as long as two hours may occur.

In the practice of this invention, a free radical aqueous emulsion copolymerization of 1,3-butadiene and styrene initiated through the use of an oxidant prepared by treating the more harshly derived monohydroperoxide composite distilland according to the method of this invention had an overall reaction time, without appreciable induction time, comparable to such a copolymerization initiated with a commercially obtainable mixture of m- and p-diisopropylbenzene hydroperoxide as the redox catalyst oxidant. Therefore, the treatment of the properly refined product made by the more harsh oxidation of p-diisopropylbenzene was deemed successful in that it demonstrated a high grade free radical initiator could be achieved.

The hydroperoxide equivalent concentration can be conveniently determined (ASTM No. E-298-68) on the hydroperoxide oxidant composite. By this measure the analysis assumes that all of the hydroperoxide is in the monohydroperoxide form although it is acknowledged that a portion thereof is dihydroperoxide.

The emulsion polymerization itself is conducted in conventional manner utilizing conventional emulsifying agents for emulsifying the monomer and product and modifiers such as various mercaptans. The pH of the aqueous phase is conventionally in the range of about 3 to about 12. Conventional reaction times and temperatures are used. The actual redox catalyst itself is generated in situ by reacting the oxidant with conventional reducing agents such as ferrous pyrophosphate, hydrosulphite of an alkali metal such as sodium or potassium, sodium formaldehyde sulphoxylate, various amines such as tetraethylene pentamine and chelated ferrous iron as well as other reducing agents such as ferrous sulfate and ferrous chloride.

Various monomers can be polymerized or copolymerized according to the free radical aqueous emulsion system of this invention such as those having the structure $CH_2\!=\!C\!<$. Representative of such monomers are conjugated dienes such as 1,3-butadiene, 2,3-dimethyl-1,3-butadiene, isoprene, piperylene and chloroprene, and particularly such conjugated dienes in a copolymerization with allyl olefins such as styrene, alpha-methyl styrene, p-chlorostyrene, and the like; acrylic and substituted acrylic acids and their esters, nitriles and amides, such as acrylic acid, methacrylic acid; methyl acrylate; ethyl acrylate; and methyl hexyl acrylate as well as vinyl acetate, vinyl chloride and vinylidene chloride.

Particularly preferable monomers are 1,3-butadiene, styrene and particularly the combination of butadiene or isoprene with styrene. Usually, in these cases, it is preferred to use relative ratios of butadiene to styrene in the range of about 65/35 to about 90/10 by weight.

The practice of this invention is further illustrated by reference to the following examples which are intended to be representative rather than restrictive of the scope of the invention. Unless otherwise indicated, all parts and percentages are by weight.

EXAMPLE 1

Rubbery copolymers of butadiene and styrene were produced by aqueous emulsion, free radical initiated, polymerization at 10° C. using the following recipe of Table 1:

Table 1

| Material | Parts |
|---|---|
| 1,3-Butadiene | 75.0 |
| Styrene | 25.0 |
| Tertiary $C_{12}$ mercaptan | 0.20 |
| Water | 200.0 |
| Potassium salts of disproportionated rosin acids | 2.25 |
| Tallow fatty acids | 2.09 |
| Sodium hydroxide | 0.27 |
| Sodium salt of condensed naphthalene sulfonate | 0.10 |
| Trisodium phosphate | 0.40 |
| Ferrous sulfate heptahydrate | 0.04 |
| Sulfuric acid | Trace |
| Tetrasodium salt of ethylenediaminetetraacetic acid | 0.02 |
| Potassium pyrophosphate | 0.064 |
| Sodium formaldehyde sulfoxylate | 0.024 |

Table 1-continued

| Material | Parts |
|---|---|
| Oxidant[1] | 0.12 |

[1]Some of the copolymers were made with a hydroperoxide composite prepared according to the method of this invention and some with a mixture of p- and m-diiso-propyl benzene hydroperoxides obtained as DIBHP from the Hercules Chemical Company containing approximately 50% as monohydroperoxide. Slight adjustments in the amounts of oxidants for slightly varying hydroperoxide contents were made so that equivalent amounts of oxidants were used.

In the following Table 2 is compared the use of oxidants with induction times and rates of conversion for aqueous emulsion copolymerizations of 1,3-butadiene/styrene with a recipe of the type shown in Table 1.

Table 2

| | Oxidant | Induction | Rate of Conversion |
|---|---|---|---|
| A | Distilland[1] diluted with methanol | 2 hrs | after induction, 10% hr |
| B | Liquid phase[2] from (E) (filtered solution in octane) | 35 min | after induction, 10%/hr |
| C | Organic phase[3] after 2 caustic washes | none | 10%/hr |
| D | Commercial oxidant[4] | none | 10%/hr |

[1]Distilland from step (B) described in the specification.
[2]Liquid phase from step (F) described in the specification where the saturated hydrocarbon used was n-octane in an amount of about 200 parts by weight per 100 parts by weight distilland.
[3]Organic phase from step (H) as described in the specification where the saturated hydrocarbon used was n-octane in an amount of about 200 parts by weight per 100 parts by weight distilland and the caustic used was dilute aqueous sodium hydroxide.
[4]Mixture of m- and p-diisopropylbenzene hydroperoxides obtained as DIBHP from the Hercules Chemical Company.

The comparison of oxidant C and D in Table 2 illustrates that the oxidant prepared according to the stepwise method of this invention has an equivalent performance to the commercially obtained oxidant, whereas without the critical recovery steps, the oxidant is inferior, according to experiments A and B shown in Table 2.

EXAMPLE 2

A 50-gallon reactor was used to combine 99 pounds of n-octane and 33 pounds of distilland obtained from step (B) described in the specification. The mixture was cooled to 20° C., agitated for 15 minutes, and filtered at 18° C. using a 12" deLaval centrifuge. The filtrate, 105 pounds, was washed with an equal weight of aqueous two percent sodium hydroxide and agitated for 15 minutes. After settling for 15 minutes, the caustic phase was drained. The wash operation was repeated two more times. The organic phase was concentrated by distilling under a reduced pressure of 26 inches of vacuum at 160° C. or lower. The clear, colorless product, 45% hydroperoxide in octane, was used to conduct emulsion polymerization using the recipe of Example 1. Polymerization with commercial oxidant, obtained as a mixture of m- and p-diisopropylbenzene hydroperoxide obtained as DIHP from the Hercules Chemical Company, was used as control. The polymerization activity, with respect to onset and rate, was the same for experimental and control.

In the practice of this invention, after the first aqueous caustic treatment of the distilland containing the monohydroperoxide and concentrated oxygenated by-products containing emulsion polymerization inhibitor(s), it is taught to additionally wash the recovered organic phase with dilute caustic. In this regard, it is preferred to wash 100 parts by weight recovered organic phase with about 50 to about 400 parts weight of the dilute caustic for each washing operation after the initial caustic treatment.

While certain representative embodiments and details have been shown for the purpose of illustrating the invention, it will be apparent to those skilled in this art that various changes and modifications may be made therein without departing from the spirit or scope of the invention.

What is claimed is:

1. A method of preparing a composite suitable as an oxidizing component in a redox aqueous emulsion polymerization initiator which consists essentially of the steps of (A) obtaining the oxidation product of reacting p-diisopropylbenzene with oxygen at a temperature in the range of about 105° C. to about 120° C. to a sufficient conversion that said product has about 40 to about 70 percent hydroperoxide content according to ASTM No. E-298-68 and is comprised of a mixture of p-disopropylbenzene mono- and dihydroperoxide, unreacted p-diisopropylbenzene, and oxygenated byproducts containing aqueous emulsion diene polymerization inhibitors, (B) removing by a separation procedure, selected from at least one of crystallization and fractionation, followed by subsequent filtration, a major portion of said p-diisopropylbenzene dihydroperoxide, and treating a portion of the filtrate by fractionation to a pot temperature in the range of about 70° C. to about 110° C. to remove p-diisopropylbenzene and a portion of said p-diisopropylbenzene monohydroperoxide distillate to effect a concentration of the remainder as a distilland having an equivalent monohydroperoxide content by ASTM No. E-298-68 in the range of about 70 percent to about 90 percent comprised, by weight of about 45 to about 65 percent p-diisopropylbenzene monohydroperoxide, about 5 to about 15 percent p-diisopropylbenzene dihydroperoxide and about 10 to about 30 percent oxygenated byproducts, (C) forming a solid/liquid two-phase product by mixing with 100 parts by weight of said remainder distilland, at a temperature in the range of about 15° C. to about 50° C., about 50 to about 400 parts by weight of at least one liquid, non-polar saturated hydrocarbon selected from at least one of n-hexane, isohexane, n-heptane, isoheptane, n-octane, isoctane, n-decane, cyclopentane, cyclohexane, cycloheptane and cyclooctane (D) recovering said liquid phase by filtration, (E) treating 100 parts by weight of said liquid phase by mixing therewith, at a temperature in the range of about 15° C. to about 50° C., about 50 to about 400 parts by weight aqueous sodium or potassium hydroxide solution containing about 0.5 to about 15 weight percent sodium or potassium hydroxide and allowing the mixture to equillibrate to form an organic/aqueous two-phase product, (F) recovering said organic phase by draining or decantation, (G) treating 100 parts of the recovered organic phase one to three times with about 50 to about 400 parts by weight dilute aqueous sodium hydroxide solution containing about 1 to about 4 weight percent sodium hydroxide to form an organic/aqueous two-phase product by the method of Step (E) and (H) recovering the final organic phase.

2. The composite product of claim 1.

3. The method of claim 1 where the saturated hydrocarbon used in step (C) is n-octane.

4. The oxidant composite product of claim 3.

5. The free radical generating redox catalyst suitable for use as an aqueous 1,3-butadiene/styrene copolymerization initiator consisting essentially of a reducing component and an oxidizing component, where said oxidizing component is a composite prepared according to the method of claim 1 and where said reducing component is selected from the group consisting of at least one of ferrous pyrophosphate, hydrosulphite of an alkali metal selected from sodium or potassium, sodium formaldehyde sulphoxylate, tetraethylene pentamine, chelated ferrous iron, ferrous sulfate and ferrous chloride.

* * * * *